(12) United States Patent
Unger et al.

(10) Patent No.: US 6,627,421 B1
(45) Date of Patent: Sep. 30, 2003

(54) METHODS AND SYSTEMS FOR APPLYING MULTI-MODE ENERGY TO BIOLOGICAL SAMPLES

(75) Inventors: Evan C. Unger, Tucson, AZ (US); Yunqiu Wu, Tucson, AZ (US); Thomas McCreery, Tucson, AZ (US)

(73) Assignee: ImaRx Therapeutics, Inc., Tucson, AZ (US)

( * ) Notice: Subject to any disclaimer, the term of this patent is extended or adjusted under 35 U.S.C. 154(b) by 0 days.

(21) Appl. No.: 09/827,583

(22) Filed: Apr. 5, 2001

Related U.S. Application Data

(62) Division of application No. 09/291,502, filed on Apr. 13, 1999, now abandoned.

(51) Int. Cl.[7] .......................... C12N 13/00; C12N 15/87
(52) U.S. Cl. .............................. 435/173.5; 435/173.1; 435/173.6; 435/461; 204/450; 204/157.62; 204/600
(58) Field of Search ........................... 435/173.1, 173.5, 435/173.6, 467; 204/450, 157.62, 600

(56) References Cited

U.S. PATENT DOCUMENTS

| | | | |
|---|---|---|---|
| 5,019,034 A | * | 5/1991 | Weaver et al. ................ 604/20 |
| 5,246,437 A | | 9/1993 | Abela |
| 5,445,611 A | * | 8/1995 | Eppstein et al. ............ 604/290 |
| 5,795,755 A | | 8/1998 | Lemelson |
| 5,830,430 A | | 11/1998 | Unger et al. |
| 5,885,211 A | | 3/1999 | Eppstein et al. |
| 5,977,538 A | | 11/1999 | Unger et al. |
| 6,041,253 A | * | 3/2000 | Kost et al. ................... 600/578 |

FOREIGN PATENT DOCUMENTS

WO    WO 9740679 A1 * 11/1997 .......... A01N/43/04

OTHER PUBLICATIONS

Palumbo et al., "Targeted gene transfer in eucaryotic cells by dye–assisted laser optoporation," *J. Photoche. Photobil. B: Biology*, 1996, 36, 41–46.

Prausnitz, M.R. et al., "Methods for in Vivo Tissue Electroporation Using Surface Electrodes," *Drug Delivery*, 1993, 1, 125–131.

Stokes, H.W. et al., "A Novel Family of Potentially Mobile DNA Elements Encoding Site–Specific Gene–Integration Functions," *Integrons. Mol. Microbiol.*, 1989, 3(12), 1669–1683.

Weaver, J.C., "Electroporation: A General Phenomenon for Manipulating Cells and Tissues," *J. Cell. Biochem.*, 1993, 51(4), 426–435.

* cited by examiner

*Primary Examiner*—Jon P. Weber
(74) *Attorney, Agent, or Firm*—Woodcock & Washburn LLP

(57) ABSTRACT

A system for applying energy to cells so as to elicit the formation of pores, to enhance transfection, and/or cell transformation, includes a computer, a plurality of acoustic probes for controllably applying acoustic energy to batches of cells, and a robot operatively for effecting relative movement between the probes and the batches of cells. Preferably, the acoustic energy comprises ultrasonic energy, which is applied in combination with optical or electrical energy to enhance the formation of pores in surface membranes of the cells.

34 Claims, 8 Drawing Sheets

METHODS AND SYSTEMS FOR APPLYING MULTI-MODE ENERGY TO BIOLOGICAL SAMPLES

This Application is a divisional of U.S. provisional Application Ser. No. 09/291,502 filed Apr. 13, 1999 now abandoned.

FIELD OF THE INVENTION

The present invention relates generally to the application of energy to biological samples for the purpose of inducing transfection and cell transformation. More particularly, the invention relates to methods and systems, including a robotic system, for applying multi-mode energy, including sonic, optical and electromagnetic energy, and combinations thereof, to biological samples.

BACKGROUND OF THE INVENTION

Cells are the basic structural and functional units of all living organisms. All cells contain cytoplasm surrounded by a plasma membrane. Most bacterial and plant cells are enclosed in a rigid or semi-rigid cell wall. The cells contain DNA that may be (1) arranged in a nuclear membrane or (2) free in cells lacking a nucleus. While the cell membrane is known to contain naturally occurring ion channels, compounds that are therapeutically advantageous to cells are usually too large to pass through the naturally occurring ion channels. Conventional interventional methods for delivering compounds to cells have proved difficult in view of the need for the compounds to pass through the cell membrane, cell wall and nuclear membrane.

Molecular biology has resulted in mapping the genomes of many plants and animals including the mapping of much of the human genome. The potential for advances in the understanding of the genetic basis of diseases is great. A variety of methods have been used to insert genes into plant and animal cells. Calcium phosphate DNA precipitation has been used to deliver genetic material into cells in cell culture but efficiency of transfection and gene expression has been very low. Improved transfection has been attained with viral vectors, e.g., adenovirus and retrovirus, but difficulties with gene expression persist. In addition, substantial concerns regarding antigenicity and the potential mutagenic effects of mutant viruses exist. Liposomes, manufactured more easily than viral vectors, have shown promise as gene delivery agents. Liposomes have less biological concerns (e.g., nonantigenic) but the efficiency of transfection and gene expression using liposomes has generally been lower than with viruses.

Electroporation and sonoporation involve the application of energy to enhance transfection of genetic material into cells. For example, electroporation concerns the formation of surface "pores" to allow permeation of macromolecules into cells in the presence of an electric field. Sonoporation, on the other hand, involves the application of ultrasound to enhance transfection of genetic material into cells. There are numerous exemplary practical applications of such techniques, including screening, experimental, pharmaceutical manufacturing, and the like. Further background on sonoporation can be found in U.S. patent application Ser. No. 08/841,169, filed Apr. 29, 1997, "Methods for Delivering Compounds Into a Cell," the content of which is hereby incorporated by reference in its entirety.

Electroporation has been studied extensively and reviewed in a number of publications. See, for example, Weaver J C, Journal of Cellular Biochemistry, (1993 April) 51 (4) 426–35. Although DNA introduction is the most common use, electroporation of isolated cells has also been used for: introduction of enzymes, antibodies, and other biochemical reagents for intracellular assays; selective biochemical loading of one size cell in the presence of many smaller cells; introduction of virus and other particles; cell killing under nontoxic conditions; and insertion of membrane macromolecules into the cell membrane. More recently, tissue electroporation has begun to be explored, with potential applications including: enhanced cancer tumor chemotherapy, gene therapy, transdermal drug delivery, and noninvasive sampling for biochemical measurement. As presently understood, electroporation is an essentially universal membrane phenomenon that occurs in cells and artificial planar bilayer membranes. For short pulses (microsecond to millisecond), electroporation occurs if the transmembrane voltage, U(t), reaches 0.5 to 1.5 V. In the case of isolated cells, the pulse magnitude is $10^3$ to $10^4$ V/cm. These pulses cause reversible electrical breakdown (REB) accompanied by a tremendous increase in molecular transport across the membrane. Reversible electrical breakdown results in a rapid membrane discharge, with the elevated voltage U(t) returning to low values within a few microseconds of the pulse. Membrane recovery can, however, be orders of magnitude slower. An associated cell stress commonly occurs, probably because of chemical influxes and effluxes leading to chemical imbalances, which also contribute to eventual survival or death.

As mentioned, sonoporation involves the use of ultrasound to enhance transfection of genetic material into cells. This phenomenon is believed to be due to mechanisms involving facilitation of uptake and molecular rearrangement of DNA to promote transcription and translation. To make more efficient use of this discovery, it would be beneficial to adapt the sonoporation technique to large scale and/or miniaturized and/or high-throughput screening of samples. One aspect of the invention described herein has utility for genomics library screening, large-scale transfection of cells, and other specialized operations where the ability to achieve high levels of transfection in a short time and in high quantity is desirable.

SUMMARY OF THE INVENTION

Accordingly, the present invention addresses the need for improved methods and systems for applying energy of various types to biological materials so as to promote the formation of "pores" and thus transfection and/or cell transformation. The invention also encompasses the use of dual function transducers allowing for either electroporation or ultrasound-mediated transfection, or a combination of both ("sonoelectroporation"), to significantly increase the potential for successful cell transformation.

In one embodiment, the present invention provides a robotic system for applying energy to cells so as to elicit the formation of pores, transfection, and/or cell transformation. The inventive system includes a computer, a plurality of acoustic probes coupled to the computer for controllably applying acoustic energy to batches of cells, and a robot coupled to the computer for effecting relative movement between the probes and the batches of cells. The present invention also encompasses an automated method for applying energy to cells, comprising the use of a computer, a robot and a plurality of acoustic probes to controllably apply acoustic energy to batches of cells and to effect relative movement between the probes and the batches of cells.

In another embodiment, the present invention provides a sonoelectroporation method comprising the application of ultrasonic energy in combination with electrical energy to cells so as to enhance cell uptake of a desired material and to also enhance subsequent gene expression.

In yet another embodiment the present invention provides a method of applying energy to cells to elicit formation of pores and to enhance transfection. The inventive method comprises the use of a first energy source to elicit pore formation and the use of a second energy source to enhance transfection. The first energy source may be any one of the group consisting of ultrasound, electricity, optical and magnetic energy, and the second energy source may be any one of the group consisting of ultrasound, electricity, optical and magnetic energy, provided the first and second energy sources are not identical.

Other aspects of the present invention are disclosed below.

DETAILED DESCRIPTION OF PREFERRED EMBODIMENTS

I. Overview

Figure 1:
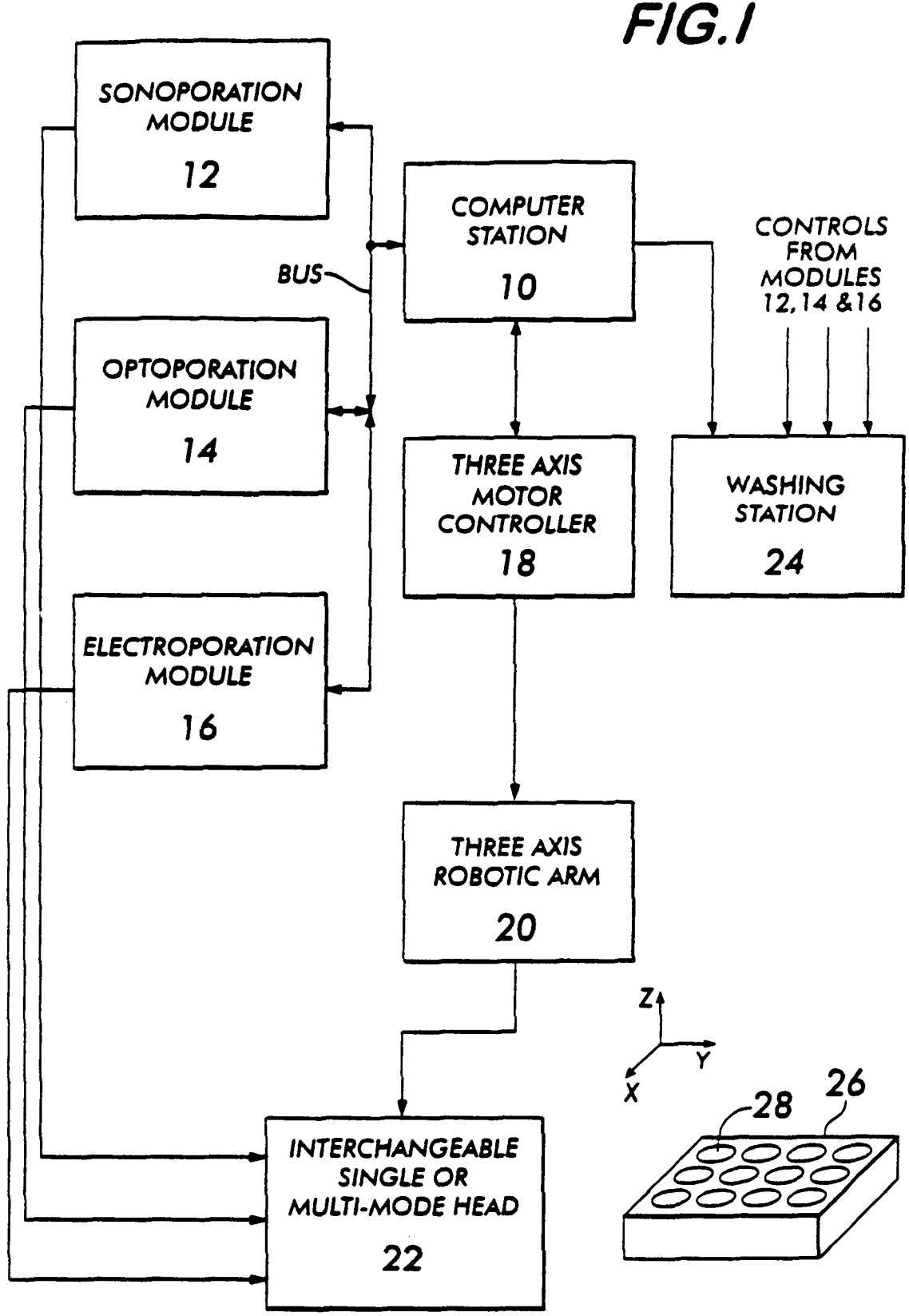
FIG. 1 schematically depicts a presently preferred embodiment of a robotic system in accordance with the present invention.

The multi-modal energy useful in accordance with the present invention provides a synergistic effect in enhancing transfection and cell transformation. Thus, increased transfection and cell transformation observed with multi-mode energy is greater than the sum of the individual energies.

In one preferred embodiment, the present invention provides a robotic system for exposing cells to energy. The energy is preferably delivered in the form of waves, either electromagnetic (electrical and/or magnetic), mechanical (including sonic), optical, or combinations thereof. Ultrasound is a preferred form of energy and may be applied to the cells for varying time durations and at varying intensities. The ultrasonic energy is preferably applied in combination with optical energy (sonooptoporation) or electrical energy (sonoelectroporation) to enhance the formation of pores in the surface membranes of the cells and to thereby facilitate permeation of macromolecules into the cells.

Although the present invention is described herein with reference to a robotic system for applying multi-mode energy to cells, where the multi-mode energy is delivered by sonooptoporation or sonoelectroporation, it is not limited to any one of these embodiments. For example, the sonoelectroporation techniques described below may be utilized without the robotic system. The converse is also true, i.e., the robotic system may be used with single mode energy (e.g., sonoporation) or some form of multi-mode energy (e.g., sonooptoporation) other than sonoelectroporation.

II. Robotic System for Multi-mode Poration

As mentioned, the present invention is perhaps most advantageously embodied in a robotic system for applying ultrasonic energy in combination with either optical or electrical energy to cells. The ultrasound may be applied in a variety of ways, depending on the particular application. The duration, frequency, mode (pulsed or continuous), intensity, etc., of the energy may be varied as necessary for a given application.

For example, the ultrasound may be applied to the cells for as little as a few milliseconds to as long as several minutes. The preferred exposure duration, however, is usually between about 500 milliseconds and about 30 seconds.

Varying frequencies of sound, from about 10 kHz to about 100 MHz, may be employed. In general, a preferred range of frequency for the ultrasound is between about 500 kHz and 5 MHz with 1 MHz being most preferred.

The ultrasound may be applied in continuous wave or in pulsed mode. The pulsing may be swept along a frequency range, e.g., PRICH or CHIRP pulses may be employed. This may be accomplished by using a broadband transducer and sweeping the transducer through the frequency range of the bandwidth of the transducer with a pulse function generator. For pulsed applications, pulse repetition frequency ranges from 0.01 Hz to 10 kHz, with a preferred range of 0.03 Hz to 1 kHz and a duty cycle between 0.1 and 99.9%, preferably 5 to 50%.

Further, more than one frequency of sound may be employed, e.g., 20 kHz with 1 MHz or 250 or 500 kHz with 1 MHz. When more than one frequency of sound is applied to the cells, the pulsing of the different frequency components is preferably modulated such that additive effects are optimized through interaction of the different frequency components. For example, the time duration between application of one or more pulses of 20 kHz and subsequent application of 1 MHz is adjusted so that the higher frequency waves arrive at a time t, where $t=\lambda/4C$ at 20 kHz, where $\lambda$ is the acoustic wavelength in the medium and C is the speed of propagation of sound in the medium.

The ultrasound intensity is preferably applied over a range from about 1 microwatt/cm$^2$ to 100 watts/cm$^2$, with the range of 0.1 to 5 watts/cm$^2$ most preferred. The ultrasound energy's peak pressure may vary from about 1 Pascal up to about 1,000 MegaPascals with the range of from about 50 kiloPascals to 50 MegaPascals most preferred.

A robotic system in accordance with the present invention will now be described with reference to FIGS. 1, 2A, 2B, 3A and 3B. (FIGS. 4–11 are more specifically directed to devices designed for use in sonoelectroporation.) As shown in FIG. 1, a system in accordance with the present invention comprises a computer station 10 and a combination of modules for applying energy of different types to batches of cells. The system of FIG. 1 includes a sonoporation module 12, an optoporation module 14, and an electroporation module 16. A three-axis motor controller 18 and a three-axis robotic arm 20 are used to permit the computer to control the movement of an interchangeable single or multi-mode head 22 in three dimensions. An optional washing station 24 may also be provided. As discussed below, the washing station may be used to prevent cross-contamination among the samples. The samples are represented schematically in FIG. 1 by a tray 26 containing multiple wells 28, which contain the batches of sample material.

Figure 2A:
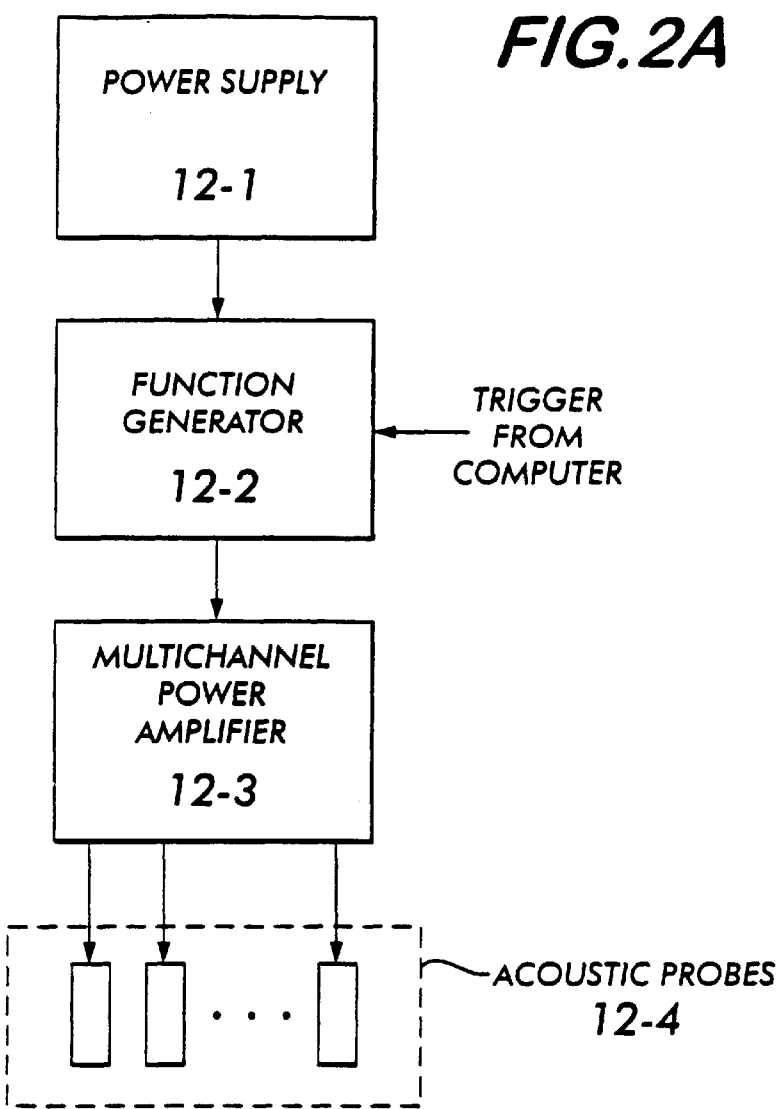
FIG. 2A schematically depicts a sonoporation module of the kind which may be employed in practicing the present invention.

An exemplary sonoporation module 12 is depicted in FIG. 2A. This module includes a power supply 12-1, a function generator 12-2, a multi-channel power amplifier 12-3 and head containing multiple acoustic probes 12-4. A ventilation system (not shown), including temperature detection and protection circuitry and a fan, may also be included for heat dissipation. The module 12 may be provided as a plug-in card that can be inserted into an expansion slot of the computer 10, or as an externally attached module. Thus, the bus depicted in FIG. 1 may be an internal or external bus. All that is required is that it provide an appropriate means by which the computer station 10 can control the respective modules.

Figure 2B:
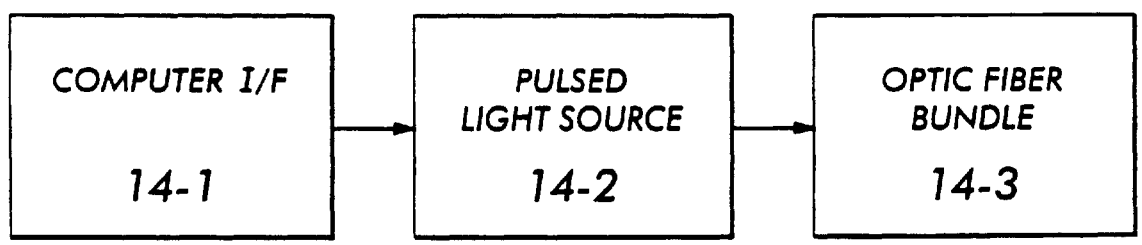
FIG. 2B schematically depicts an optoporation module of the kind which may be employed in practicing the present invention.

FIG. 2B schematically depicts an exemplary optoporation module. This module includes a computer interface circuit 14-1, a pulsed light source 14-2, and an optic fiber bundle 14-3. The computer interface circuit may include, e.g., an RS232 interface (serial port) or an IEEE-488 interface (parallel port). The pulsed light source 14-2 may include, e.g., a pulser circuit and a laser diode adapted to provide optical energy to the optic fiber bundle 14-3.

Figure 3A:
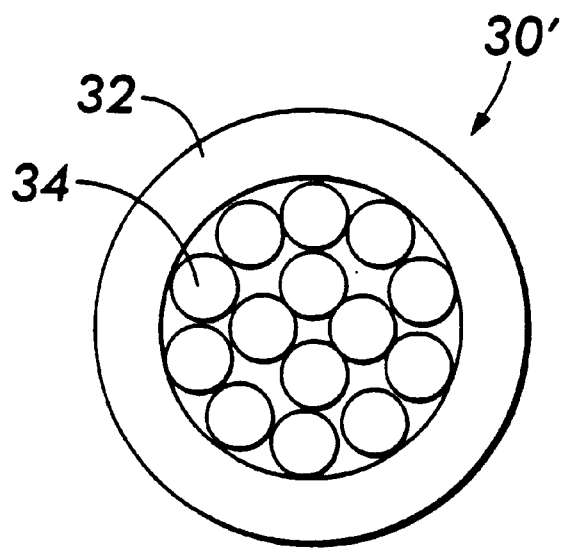
FIGS. 3A and 3B schematically depict alternative embodiments of an optoacoustic probe of the kind which may be employed in practicing the present invention.
Figure 3B:
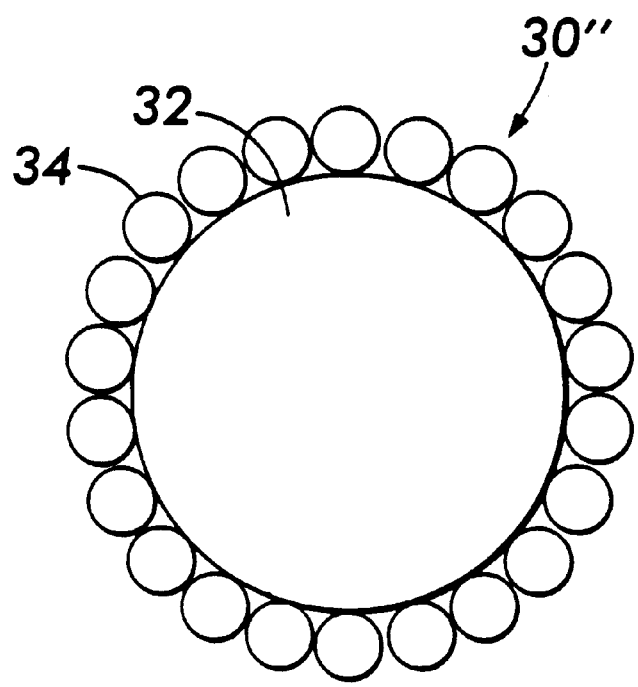

As mentioned above, the single or multi-mode head 22 (FIG. 1) will carry one or more probes for applying energy of various types to the samples. One example of a multimode, optoacoustic probe 13' is depicted in FIG. 3A. In this example, the probe includes an acoustic element 32 and a bundle of optical fibers 34. In an alternative embodiment, depicted in FIG. 3B, a probe 30" includes an acoustic element 32 and fiber elements 34 disposed around the periphery of the acoustic element. Further information about the construction of probes of this type may be found in copending U.S. patent application Ser. No. 09/075,567, filed May 11, 1998, entitled "Optoacoustic Imaging System."

Particularly for applications involving multiple samples, as exemplified with a 96-well plate, it is desirable to apply energy (e.g., ultrasound) to multiple wells simultaneously. The present invention can utilize a multihead transducer (as shown in FIG. 1) to insonate 8–96 samples at a time, preferably in multiples of 8, with the robot moving the multihead transducer to the next row of wells or the next 96-well plate. This modification accelerates the sonoporation procedure by at least a factor eight over the robotic single head transducer, allowing for greater synchrony in sample response.

The energy can be applied continuously and simultaneously to each well using a simple voltage splitter. Alternatively, in pulsed mode, energy can be applied to each sample simultaneously or sequentially. Typically, a 2.5 mm piezoelectric element will be housed within a housing ring that just fits the interior diameter of each well, which is typically 2 cm.

As discussed above, although ultrasound is a preferred energy source for activating the cells, other energy sources may also be used. When other energy sources are employed, this is preferably done in concert with ultrasound. Optical energy may be applied using a range of light sources. Most preferred is the laser light source, particularly in the infrared wavelengths when penetrability of the plate material is a limiting factor. For other applications, shorter wavelengths, e.g., ultraviolet, may be desirable for activating and deactivating biological systems or chromophores.

When designing culture plates for optimal use with the invention, the following should be considered. Where ultrasound is employed with light, the transducer ensemble is designed to contain both optical and sound elements. Preferably, the light and sound are pulsed in unison and are phase and amplitude modulated coherently. The invention may be practiced in transparent as well as opaque (black and white) plates with clear bottoms to accommodate irradiation from below.

Palumbo, et. al., (J. Photochem. Photobiol. B, 1996) used a high energy focused argon laser beam to enhance gene transfer. The laser light was believed to have induced local temperature changes which modified cell membrane permeability. When an electric field is combined with an optical field (electrooptoporation), cell permeability can be enhanced, with an instantaneous cooling of the transient pore, thus retaining greater cell viability than optical methods alone. In optoporation, because pore-forming is a thermal phenomenon, the pore may persist several minutes after the laser beam is turned off. Cell contents and solutes could equillibrate across the pore, destroying in situ gradients. In the presence of an electric field, the potential difference across the membrane drives charged macromolecules such as DNA into the cell, and the pore can "reseal" momentarily after the electric field is removed. Another advantage of the combined modalities is that a lower intensity of light is needed for gene transfer, and high-throughput applications are possible.

Targeted gene transfer can also be obtained using combined energy modalities such as electrooptoporation or variants such as magnetoporation, electromagnetoporation, optosonoporation, electrooptosonoporation and magnetosonoporation. In optoporation, a high intensity focused laser beam is needed, providing the advantage of focusing gene transfer to the single cell level if desired, as in oncological applications. However, large area irradiation is difficult. In combination with other energy sources, the intensity of light can be significantly lowered, and the area of irradiation can be widened.

A general procedure for the operation of combined modality "poration" is as follows: First apply an applicable absorptive dye into the cell culture medium, topically, transdermally or intravenously (IV). Select a light source with a wavelength peak corresponding to the absorption spectra of the dye, or vice-versa. Enhanced gene transfer will then be targeted to the cells in proximity to or having incorporated the dye upon irradiation. DNA can then be delivered from vehicles as previously described in U.S. patent application Ser. Nos. 08/841,169, filed Apr. 29, 1997, "Methods for Delivering Compounds Into a Cell"; 09/075,343, filed May 11, 1998, "Novel Acoustically Active Drug Delivery Systems"; and 09/075,477, filed May 11, 1998, "Solid Porous Matrices and Method of Making and Using the Same", the disclosures of each of which are incorporated herein by reference in their entirety. Next, an electric or acoustic or magnetic field is applied to the irradiated area either simultaneously (preferred) or subsequently.

The equipment used for the above will depend on the application. Lamps can be used to replace lasers when the light intensity requirement permits. The device in simplest form comprises a probe (e.g., ultrasound or optoacoustic), a computer, a manifold for actuating movement of either the probe or the sample platform, actuators comprising electronics to bridge the output of the computer to the production of ultrasound energy or electromagnetic energy and accessories.

The mechanical manifold can be of any mechanism that controls and provides a combined mechanical movement in three dimensions (x, y, and z and angular directions). The mechanical driver or motor can be any of a number of devices widely known in the art, e.g., a PI-C-560 stepping motor controller with an M-413 linear positioner and M-038.00 rotary positioner equipped with an M-441.30 stepping motor drive (Physik Instruments, Waldbronn, Germany). The controlling manifold can be a stand-alone component. It can also be a plug-in board such as a PIC-812 DC motor controller, which fits into an extension port of the computer. The mechanical manifold can be of a stand-alone or a plug-in type. One example of the latter is a TB-100 Gated Amplifier Tone Burst Plug-In card (Matec, Northborough, Mass.), which drives an ultrasound transducer.

The probe component comprises one or more of a set of modalities (ultrasound, electricity, magnetism, optics) of which the ultrasound modality is the most preferred. When the probes are used in combination, they can be physically separated for applying treatment to separate wells on the sample plate or used simultaneously on a given sample well. Ideally the probe head is of a type which can be immersed, but in some applications it may beneficial, even preferable, to have the probe tip contact a membrane which separates the biological sample from the probe. For situations where close contact of the probe tip with the sample is required, three general methods may be used to avoid cross-contaminating samples. In one method, a washing station comprising a pump manifold and an adjoining reservoir can be used to wash the probe. The second preferred alternative utilizes a disposable membrane covering the sample, and finally the probe head may be applied from the bottom with a special plate/membrane combination.

The electronics/optics component excites or actuates the probe head in order to generate acoustic waves, electromagnetic energy or fields, optical waves or a combination thereof. This component includes a pulser, an amplifier and an optional interface. The use of an interface is preferred so that the computer can communicate with the component and control output power, amplitude, frequency, energy and pulse shape generated by the probe component. However, the electronics/optics component comprising only a pulser and amplifier will suffice to perform the functions of the invention.

For preferred ultrasound applications in particular, the probe head comprises an ultrasound transducer excited in PW or CW mode (pulsed or continuous). To determine the fluid level, the pulsed wave is first used to generate a short soundwave, and the reflected echo is detected by a receiver. Based upon the difference in time between the transmitted pulse and the received echo, the sample fluid level can be determined by:

$$\Delta h_{(cm)} = L_{(cm)} - 1.70(t), \text{ with t in microseconds.}$$

After calculation of the sample fluid level, a transducer can be put into contact with the sample surface and the center frequency, sound intensity, treatment time, wave mode (continuous or pulsed) and other parameters can be programmed and controlled by the computer. The operator can use direct memory access (DMA) or other methods to interrupt treatments and change parameters manually. Preferably for most operations, the frequency is between 10 kHz and 50 MHz, more preferably 50 kHz to 10 MHz, and most preferably from 100 kHz to 6 MHz. For most applications, single element transducers will suffice, however, it is possible to employ two elements in one trasducer probe. Preferably, the two elements will have different center frequencies. Preferably, one element will have a lower frequency, $f_1$, in the range of 20 kHz to 3 MHz; and the second element will have a higher center frequency, $f_2$, preferably in the range of 100 kHz to 6 MHz. Depending on the nature of the medium under treatment, it may be desirable for $f_2$ to be an integer multiple of $f_1$ ($nf_1 = f_2$, where n is a positive integer). The intensity level is preferred to be 0.1 W/cm$^2$ to 100 W/cm$^2$, more preferably 0.2 W/cm$^2$ to 10 W/cm$^2$, and most preferably 0.2 W/cm$^2$ to 5 W/cm$^2$. Duration of treatment is preferably between 10 seconds and 10 minutes. Duty cycle can be varied between 0.1% to 99.9% with a pulse repetition frequency of about 1 kHz+/−0.1 Hz.

For optical probes, light wavelengths between 195 nm to 2500 nm are well within the capabilities of the instrumentation, with intensities between $10^{-5}$ W/m$^2$ to $10^3$ W/m$^2$.

Optionally, a barcode reader is incorporated into the robotic device to achieve high throughput or high capacity.

I.1 Biology

It has previously been shown that ultrasound influences genetic expression levels in living cells (see U.S. patent application Ser. No. 08/971,540, filed Nov. 17, 1997, entitled "A Method of Increasing Nucleic Acid Synthesis With Ultrasound"). This effect is manifested in both native (also known as "endogenous") genes in the form of genetic up-regulation, particularly of repair and housekeeping genes, and in increasing the rate and extent of transfection of exogenously delivered genetic material.

The present invention is useful for enhancing exogenous gene expression in a wide variety of cells. "Cell" and "host cell" refer to prokaryotic cells and eukaryotic cells, including plant cells, animal cells, cells of unicellular organisms, cells of multicellular organisms, etc. Especially preferred are animal cells, more preferably mammalian cells and most especially human cells, including but not limited to living cells, tissues, and organs. Eukaryotic cells are cells of higher organisms in which genetic material is enclosed by a nuclear membrane. Prokaryotic cells are cells of lower organisms that lack a well defined nucleus and contain genetic material that is not enclosed within a membrane of its own. The cells may be present in vivo or in vitro (e.g. in cell culture). Eucaryotic cells include, for example, mammalian, avian, reptilian, amphibian, invertebrate, protists, algae, fungi and the like. Procaryotes refer to bacteria and blue-green algae.

The invention has wide applications for increasing (promoting, facilitating or enhancing) nucleic acid synthesis in both in vitro and in vivo applications, and is particularly useful for prokaryotic and eukaryotic animal cells, particularly mammalian cells. Intracellular delivery includes delivery into the cells through a cell membrane (plasma membrane), cell wall, and/or nuclear membrane. In the case of exogenous nucleic acid sequences, the efficiency of intracellular delivery (e.g., transfection) of such nucleic acid sequences is also increased.

The phrase "cell membrane" (also termed "plasma membrane") is used in its conventional sense as denoting the outer layer or boundary of the cytoplasm of a living cell. Cell membranes are typically comprised of protein and lipids, and are generally found in animal cells.

The phrase "cell wall" is also used in its conventional sense to denote a rigid or semi-rigid outer covering surrounding the protoplasts of plant cells and most prokaryotes. Cell walls are typically found, for example, in cells of bacteria, plants, algae, and fungi. Cell walls are, on the other hand, generally not present in animal cells. In plants, the wall typically comprises several layers; a primary wall composed of cellulose microfibrils running through a matrix of hemicelluloses and pectic substances surrounded by a secondary wall composed of cellulose which is generally lignified to a varying extent. Cell walls of fungi may contain varying amounts of chitin. Cell walls of prokaryotes are typically strengthened by mucopeptides and may be surrounded by a mucilagenous capsule.

"Nucleic acid" and "nucleic acid sequence" include nucleotides, nucleosides, DNA including genomic DNA and cDNA, RNA, antisense sequences, oligonucleotides, and the like. Single and double stranded nucleic acid sequences, including and not limited to oligonucleotide sequences of about 100 kb to about 1,000,000 kb (including whole chromosomes), preferably of about 4 kb to about 6 kb, more preferably about 1,000 nucleotides in length, more preferably about 500 nucleotides in length, more preferably about 250 nucleotides in length, more preferably about 100 nucleotides in length, more preferably about 50 nucleotides in length, more preferably about 25 nucleotides in length, more preferably about 10 nucleotides in length, even more preferably about 3 kbp to about 10 kbp in length, are contemplated by the present invention. Embodied by the term "nucleic acid sequence" are all or part of a gene, at least a portion of a gene, a gene fragment, a sense sequence, an antisense sequence, an antigene nucleic acid, a phosphorothioate oligodeoxynucleotide, and an alteration, deletion, mismatch, transition, transversion, mutation, conservative substitution, and homolog of a sequence. The phrase "at least a portion of," and "all or part of," as used herein, means that the entire gene need not be represented by the sequence so long as the portion of the gene represented is effective to block or exhibit, depending on the type of sequence used, gene expression. The sequences may be incorporated into an expression vector such as, and not limited to, a plasmid, phagemid, cosmid, yeast artificial chromosome (YAC), virus (e.g., adenovirus, vaccinia virus, retrovirus), and defective virus (also known as a "helper virus"). The nucleic acid sequence may also be administered naked, that is without an expression vector.

Variations in the nucleic acid and polypeptide sequences of the present invention are within the scope of the present invention and include N terminal and C terminal extensions, transcription and translation modifications, and modifications in the cDNA sequence to facilitate and improve transcription and translation efficiency. In addition, mismatches within the sequences identified herein, which achieve the methods of the invention, such that the mismatched sequences are substantially complementary to the sequences identified, are also considered within the scope of the present invention. Mismatches which permit substantial complementarity to particular sequences, such as similarity in residues in hydrophobicity and hydrophilicity, will be known to those of skill in the art once armed with the present disclosure. In addition, the sequences of the present invention may be natural or synthetic. Homologs and alternatively spliced sequences and fragments of the sequences which are substantially similar or have substantially the same activity of the sequences of the present invention are also contemplated herein.

In the case of exogenous nucleic acid sequences and in accordance with the methods of the present invention, the synthesis of any nucleic acid sequence added to a cell is increased by ultrasound. Accordingly, nucleic acid sequences encoding stress proteins, repair proteins, as well as structural proteins, proto-oncogenes, and regulatory proteins, for example, exhibit increased synthesis upon administration of the same and ultrasound to a cell. Structural nucleic acid and protein sequences encode products, such as protein, enzymes, tRNA, as opposed to a nucleic acid or protein sequence that serves a regulatory role. Proto-oncogenes are the normal, cellular equivalent of an oncogene, involved in the signaling or regulation of cell growth. An oncogene is a mutated and/or overexpressed proto-oncogene of animal cells that in a dominant fashion releases the cell from normal restraints on growth, and alone, or in concert with other changes, converts a cell into a tumor cell. Proto-oncogenes useful in the present invention include and are not limited to c-fos, c-myc, c-jun, and jun-b. Regulatory nucleic acid sequences encode molecules controlling the sequencing or expression of a gene, and include promoters, enhancers, and the like.

Methods of introducing exogenous sequences into a cell (also referred to variously herein as methods for delivering a sequence into a cell, methods of intracellular delivery, methods of promoting, effecting, facilitating or enhancing the uptake of a sequence into a cell, and the like) include "transfection", which refers to the introduction of genetic material, i.e., a nucleotide sequence (e.g., DNA or RNA) into a host cell. Transfection is also sometimes referred to as transformation. DNA (or RNA) which is new to the cell into which it is incorporated is typically referred to as heterologous DNA (or RNA) or exogenous DNA (or RNA). Some bacterial species take up exogenous DNA and do not discriminate between uptake of DNA from a similar or same species or from a completely different species or organism. Exogenous DNA may also be taken up by cells, but may or may not be incorporated into nuclear material in a heritable manner. The objective of transfection of a host cell may be to effect expression of one or more carefully selected sequences.

Increased synthesis refers to transcription and/or translation of a nucleic acid sequence resulting in the production of an amino acid, peptide and/or protein. In the case of exogenous sequences, administration of the nucleic acid sequence and multi-mode energy results in increased synthesis of the sequence as compared to conventional transfection techniques such as calcium phosphate precipitation, viral vectors, microinjection, shock wave such as for example lithotripsy, and electroporation, may be increased. Methods of measuring increased nucleic acid synthesis will be known to skilled artisans once armed with the present disclosure and include amplification and enzyme-linked immunosorbent assay (ELISA) as well as methods disclosed in Sambrook, et al., *Molecular Cloning: A Laboratory Manual*, 2nd ed., Cold Spring Harbor Laboratory Press, Cold Spring Harbor, N.Y. (1989), the disclosures of which are hereby incorporated herein by reference in their entirety. Thus, as a result of the methods of the present invention, a product (e.g., a nucleic acid sequence or a protein) may be produced. In addition, the prevention of the production of a product (such as, as a result of an antisense sequence delivered into the cell) by the host cell may also result.

Without being bound by any theory of operation, it is believed that multi-mode energy may also induce a cell to take up an exogenous nucleic acid sequence in accordance with the methods of the present invention. Included within the definition of delivery of a sequence into a cell in accordance with the methods of the present invention are active and passive mechanisms of cellular uptake. Ion channels and other means of transport utilized by cells to incorporate extracellular materials, including compounds to be delivered thereto, into the intracellular milieu are encompassed by the present invention.

A wide variety of nucleic acid sequences may be delivered as bioactive agents, diagnostic agents, pharmaceutical agents, and the like. Whole genes, multiple gene sequences, and gene fragments may be utilized as well as whole chromosomes and chromosome fragments.

A sonoporation initiator (SPI) can be used to increase expression of clinically important genes. In many disease states, the gene for the missing protein is present but is not produced in sufficient levels. This may be due to a poor promoter, or the protein being expressed at physiological levels but not at pharmacologic levels. The SPI that is present upstream of genes that are upregulated by treatment with ultrasound has been identified. An SPI may be defined as a region just upstream of the genes which are activated by ultrasound. The SPI has the potential to sensitize the cell to the ultrasound energy.

Integrons comprise an integrase-encoding gene which allows for site-specific insertion of resistance-gene cassettes between two highly conserved adjacent nucleotide sequences. The activity of the integrons has been shown in bacteria, insect and mammalian cells. It is possible to target specific sequences by modifying the ends of the integron DNA. See, e.g., Stokes, H. W. and Hall, R. M., "A Novel Family of Potentially Mobile DNA Elements Encoding Site-Specific Gene-Integration Functions," Integrons. Mol. Microbiol., (1989) 3(12), 1669–1684.

A sonoporation initiator integron (SPII) may be devised as follows. While not intending to be bound by any particular theory or theories of operation, the SPII will be modified so that the ends integrate with the DNA upstream of the clinically important target gene. The SPI will be inserted into the integron. The integrase of the integron will act on the DNA to insert the SPI. The inserted SPI will then be activated by ultrasound to upregulate the target gene.

The ability to rapidly and efficaciously manipulate and screen cells in which certain genes are variably operable is afforded by the parameters of the described invention.

The invention will become even clearer in view of the hypothetical examples provided below.

II.2 Exemplary (Hypothetical) Applications

Example 1. This is a procedure for transient transfection of adherent cells. In a six-well tissue culture plate, $4 \times 10^5$ cells (NIH3t3 cells, for example) are seeded in 4 mls of growth media with calf serum. The plate is incubated for 24 hrs. at 37° C. in an atmosphere with 5% $CO_2$. This procedure should produce cells to 50%–60% confluency. Lipid and DNA solutions are prepared by diluting 5 micrograms of DNA samples into 100 microliters of HEPES Buffered Saline (HBS) (HEPES–20 mmol/l, NaCl–150 mmol/l, pH 7.4). (For example, the DNA could be the CAT gene (chloraphenicol acetyltransferase) and the lipid could be DPEPC/DOPE mixture; other genes could be c-DNA encoding VEGF, interleukin-2 or insulin, just to name three that would be of practical utility.) The solutions are added to each well. Thirty microliters of transfection lipid preparation is also diluted into 100 microliters of HBS for each well. After preparing the DNA and lipid solutions, the two solutions are gently mixed by inversion 5–6 times and incubated 45 minutes at 25° C. 200 microliters of the DNA/lipid mixtures are then added to each well and the contents is agitated by pipetting slowly three times. Additional 37° C. incubation follows in a 5% $CO_2$ atmosphere for 24–72 hours. Gene expression is then assayed. The following table sets forth exemplary exposures and conditions for ultrasound energy.

| | |
|---|---|
| Ultrasound Energy Level (Range) | 1 W/cm² to 1 kW/cm² |
| Preferably | 50 mW/cm² to 50 W/cm² |
| Most Preferably | 100 mW/cm² to 10 W/cm² |
| Duration of Treatment (Range) | 1 nanosec. to 1 hr. |
| Preferably | 1 microsec to 10 min. |
| Most Preferably | 1 millisec to 2 min. |

III. Sonoelectroporation

Another combination modality for use with ultrasound as an embodiment of the present invention involves a dual probe for administration of electromagnetic energy in the UV, visible and IR spectral regions. Such energy could be useful for selective inactivation of certain genetic regions or for photo tactic responses in bacteria and/or activation of photosynthesis, among a myriad of other possibilities. To date, no publications have disclosed adapting applications of light/electromagnetic energy in the UV or IR region to biological samples via robotic mechanisms except for detectors, e.g., spectrophotometers or calorimeters.

Electrical energy may be applied to the cells. Again, the electrical energy is preferably applied in concert with ultrasound. This can be accomplished by using a specially designed sonoelectrical transducer containing electrodes within the transducer ensemble. Preferably, one or more electrical impulses are generated and then ultrasound is applied to the cells. Note also that ultrasound and electrical impulses may be applied simultaneously. The advantage of sonoelectroporation is that it enhances cell uptake of the desired material and also enhances subsequent gene expression.

For sonoelectroporation to be effective, a very strong electric field (1–10 kV/cm) is preferred. It is generally believed that the high voltage is needed in order to create a "reverse pore" through the cell membrane. The concepts behind sonoelectroporation are based on the idea that the electric field aligns components according to charge polarity, but ultrasound creates the pore. The electric energy and ultrasound combine to drive components of the medium into the cell. Releasing ultrasound allows the pore to reseal.

While not intending to be bound by any particular theory or theories of operation, it is believed that the electric field is not needed to create the pore. Because the pore forms independent of a strong electric field, the electric field intensity is significantly lower than that used in sonoelectroporation.

Figure 4A:
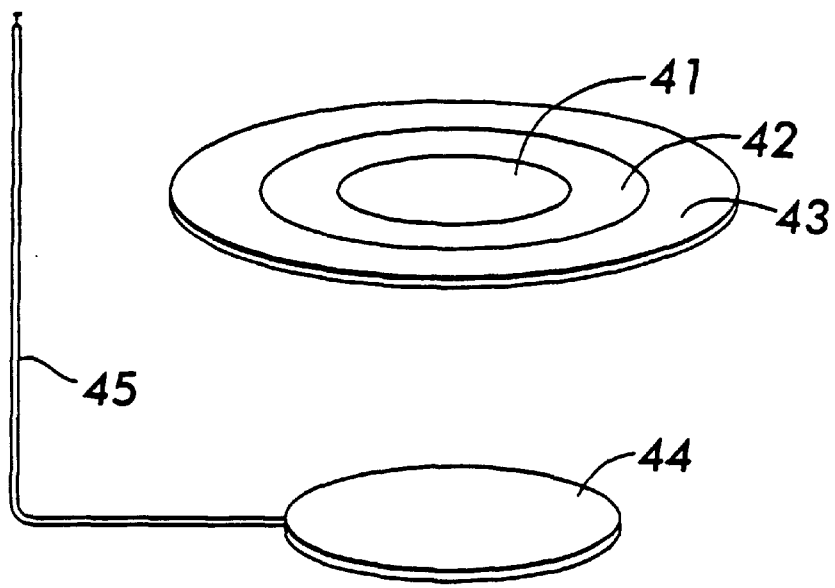
FIGS. 4A and 4B schematically depict presently preferred embodiments of a system for performing sonoelectroporation in accordance with the present invention.

FIG. 4A illustrates a sonoelectroporation system. In this system, 41 is an annular transducer element, preferably made of a ceramic; 43 and 44 are electrodes, preferably made of metals such as aluminum, stainless steel or platinum or of a conductive polymer; and 42 is insulating material to separate the transducer element 41 and electrode 43. The polarity of 43 and 44 is interchangeable. An insulated wire 45 carries electrical energy to electrode 44. Optionally, and preferably, electrode 44 is anchored by but not in physical contact with a thin film of non-conductive material such as paraffin, plastic or an agar-based polysaccharide. In the alternative embodiment depicted in FIG. 4B, the transducer head is an array of multi-electrode and acoustic elements. All cathodes and anodes are electrically connected. The polarity of the electrodes is interchangeable.

The parameters specified for the sonoelectroporation device include an acoustic element operating at a frequency between 10 kHz and 10 MHz. The mode of operation (continuous or pulsed wave) will depend on the application. Pulsed wave is preferable for applications of energy to single cells or unilamellar cell cultures. In this regard, pulsing also may act as an on/off switch. Continuous wave provides sustained delivery, but application may be limited by concomitant production of heat. It is contemplated that perfused organs, thick tissues or whole bodies may benefit most from continuous wave applications. Because either CW or PW can be used, the intensity of energy needed is to be defined as $I_{SATA}$, or spatial average/temporal average intensity. Recommended ranges of $I_{SATA}$ are 1.0 $\mu W/cm^2$ to 100 $W/cm^2$, with 0.1 to 5 $W/cm^2$ preferred. Pulse duration is preferably between 0.1 $\mu s$ to infinity (CW), with 10 $\mu s$ to 10 ms most preferred. The pulse repetition frequency ranges from zero (CW) to 20 kHz, with a range of 0.5 Hz to 1 kHz preferred. For the electrical element, the RF frequency ranges from DC to 100 MHz and preferably 100 kHz to 2 MHz. The electric field intensity should be between 1 Volt/cm to 100 kV/cm, preferably 50 V/cm to 10 kV/cm.

Figure 4B:
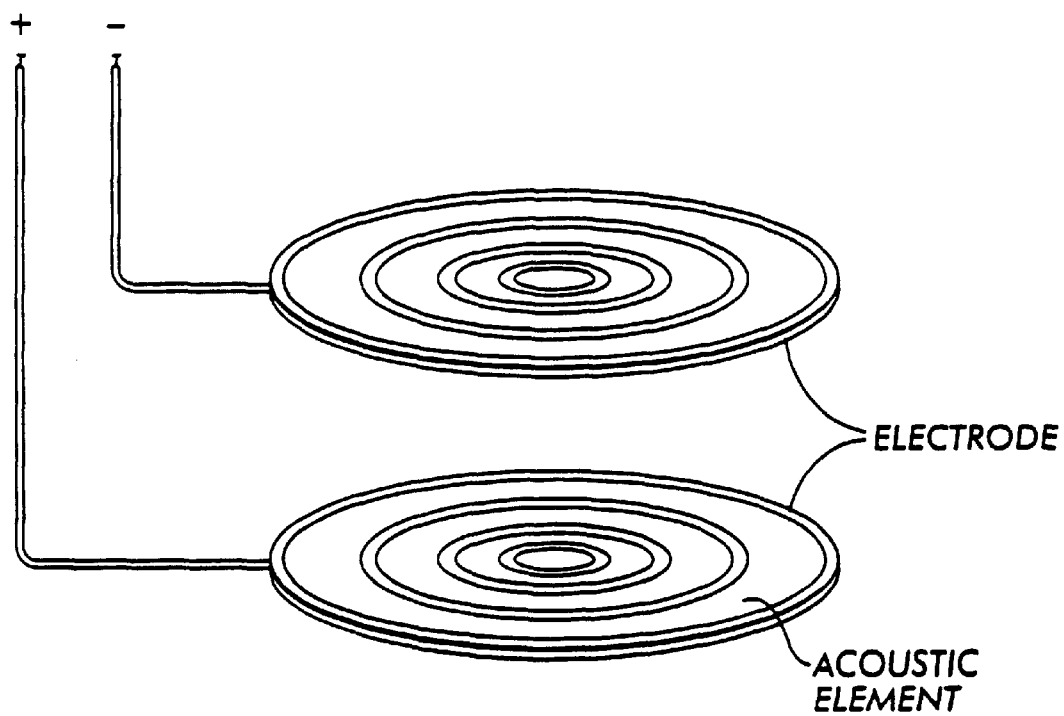
Figure 5:
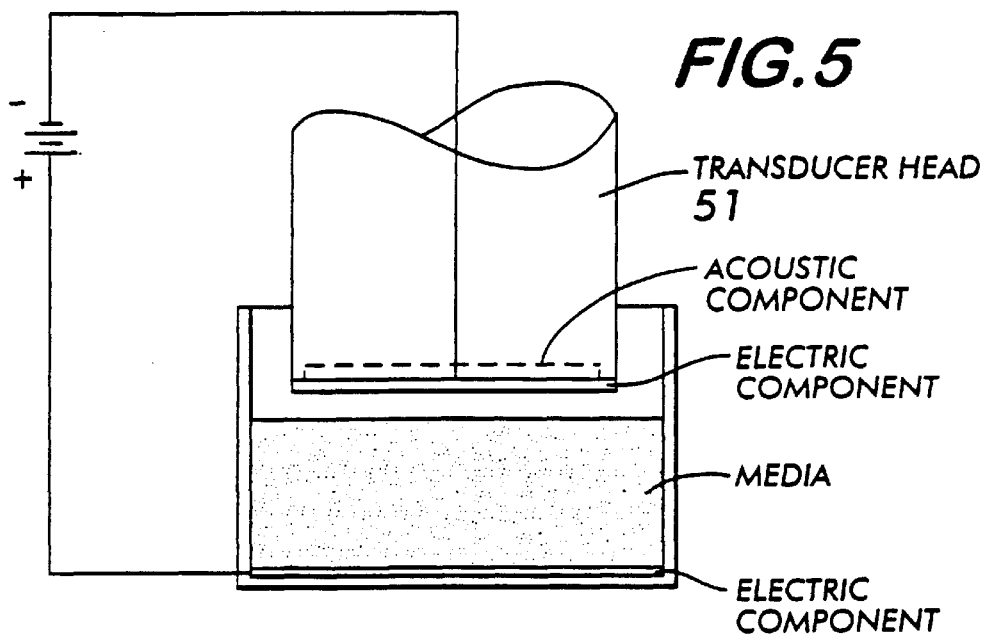
FIG. 5 illustrates an arrangement of electrodes in a culture well.

An electrical circuit inside culture wells is illustrated in FIG. 5. Note the bottom of the culture well may have electrical wires, electrical mesh or a conducting surface composed of a conducting polymer, metal or metal coated surface of metal oxide. Circuitry allows electrical current to pass from the sonoelectroporation head into the culture medium and into the cells. When performing sonoelectroporation, a transducer head similar to that shown in FIG. 4A or 4B is placed inside the culture well and proximal to but not touching the bottom electrode. The bottom electrode is the anode and the transducer head serves as the cathode. Note that the polarity may be reversed. Both, electrodes are connected to a voltage source, thus providing an electric field between the electrodes. In the arrangement shown in FIG. 5, the transducer head 51 is connected to the negative terminal of a voltage source 52, with the negative electrode 53 of the electric component situated in front of the acoustic component 54. The positive electrode 55 of the electric component is separated from the negative electrode by the culture medium 56.

Figure 6:
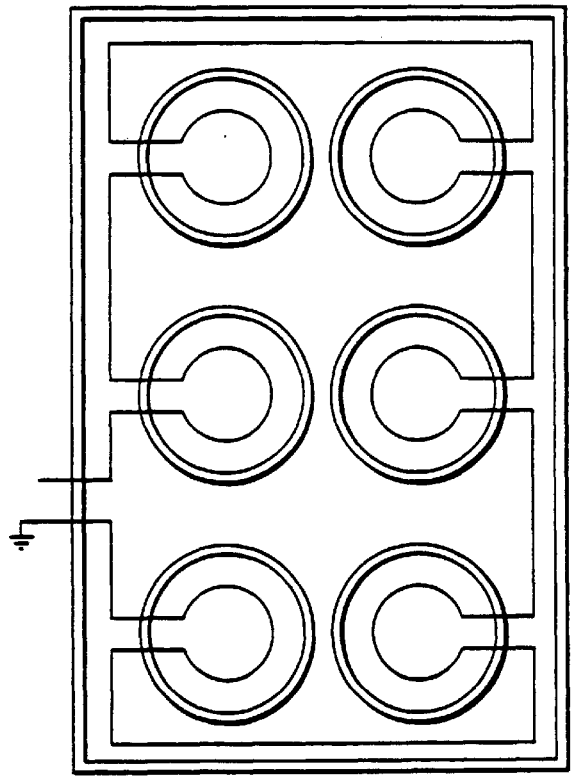
FIG. 6 depicts an overhead cross section of current elements in a multiwell plate.

The head of the sonoelectroporation device is illustrated in FIG. 6. (Note that the poles may be reversed.) The transducer head fires an electrical pulse in concert with ultrasound. Electricity is carried as discharge with the sonic wave through cell culture media. The cell culture well surface and circuitry are designed to facilitate passage of electrical discharge.

Sonoelectroporation can be applied to the body for local treatment of diseased areas and may be especially effective for application to tumors. In this regard, the use of catheters, endoscopy or angiography can be coupled to the devices described in the present invention. The practitioner should exercise care in using an isolated ground remote from the surfaces in contact with the patient.

Metals which can be used in the composition of the electrodes are listed below. Those of skill in the art will recognize that alloys made up of combinations of the listed metals will also operate as conductive materials.

Conductive Materials: Aluminum, Antimony, Arsenic, Barium, Beryllium, Chromium, Cobalt, Niobium, Copper, Cysprosium, Erbium, Gadolinium, Ballium, Gold, Hafnium, Holmium, Indium, Iron, Lanthanum, Lead, Lithium, Lutetium, Magnesium, α-Manganese. β-Manganese, γ-Manganese, Mercury, Molybdenum, Neodyrnium and Nickel.

Additionally, certain compounds having electrooptic, elastooptic or magnetooptic properties will function to conduct current and thus can be used either by themselves or as dopants in the fabrication of electrodes. Such materials include:

Electrooptic Materials of KDP- and ADP-type: $KH_2PO_4$ (KDP), $KD_2PO_4$ (DKDP), $KH_2AsO_4$ (KDA), $KD_2AsO_4$ (DKDA), $RbH_2PO_4$ (RDP), $RbH_2AsO_4$ (RDA), $RbD_2AsO_4$ (DRDA), $CsH_2AsO_4$ (CDA), $CsD_2AsO_4$ (DCDA), $NH_4H_2PO_4$ (ADP), $ND_4D_2PO_4$(DADP) and $NH_4H_2AsO_4$ (ADA).

Electrooptic Materials of $ABO_3$-type: $LiNbO_3$ (1470), $LiTaO_3$ (890), $BaTiO_3$ (395), $K_3Li_2Nb_5O_{15}$ (693), $Sr_{0.75}Ba_{0.5}Nb_2O_6$ (~330), $Sr_{0.5}Ba_{0.5}Nb_2O_6$, $Sr_{0.25}Ba_{0.75}Nb_2O_6$ (~520), $KTa_xNb_{l-x}O_3$ (~330), $PbTiO_3$ (765), $KSr_2Nb_5O_{15}$ (443), $LiIO_3$;(Pyroel.) and $Ba_2NaNb_5O_{15}$ (883).

Electrooptic Materials of AB-type: CuCl, CuBr, ZnO, ZnS, CDs, CdSe, CdTe, HgS, ZnS, ZnSe, ZnTe, GaP and GaAs.

Electrooptic Materials of miscellaneous types: $K_2Ni_2(SO_4)_3$, $NaClO_3$, $NA_3SbS_4.9H_2O$, Sodium uranyl acetate. $LiKSO_4$. $LiNaSO_4$, Tourmaline, $NA_3Li(CrO_4)_2.6H_2)$, $Ag_3AsS_3$ (Proustite)[*1], $KsS_2O_6$, $Cs_2C_4H_4O_6$, $SrS_2O_6.4H_2O$, $Se^{*2}$, $SiO_2$ (Quartz)[*3], $(C_6H_{12}O_6)_2NaBr$ $H_2O$, $AgGaS^{*4}$, $Gd_2(MoO_4)_3{}^{*5}$, $CdGa_2S_4$, $(NH_4)_2C_2O_4.H_2O$, $NaNO_2{}^{*6}$, $C(CH_2OH)_4$ and $Ca_2Nb_2O_7$.

Photoelastic Materials: Melted quartz ($SiO_2$), $As_2S_3$-glass, Dense fling (SF-4), Water, $Ge_{33}Se_{55}As_{12}$-glass, $Sb_2O_3$, Various optical glasses, Dense flint (SchottSF-59), $PbO:2sB_2O_3$, Lucite, Polystyrene, GaP, GaAs, $Y_3Al_5O_{12}$ (YAG), $Y_3Fe_5O_{12}$(YIG), β-ZnS, Ge, $ZnAl_2O_4$, $SrTiO_3$, $Y_3Ga_5O_{12}$, $Bi_4Ge_3O_{12}$, KRS-5 (Thallium bromoiodide), Diamond, LiF, MgO, KBr, KCI, KI, NaCi, $Ba(NO_3)_2$, $Bi_{12}GeO_{20}$, $Bi_{12}SiO_{20}$, $Pb(NO_3)_2$, $NaBrO_3$, $NaClO_3$, $LiTaO_3$, α-$Al_2O_3$, Te, $LiNbO_3(_p{}^E)$, Ruby ($Al_2O_3$+0.05% Cr), α-Quartz ($SiO_2$), $CaCO_3$, $Li_2WO_4$, CDs, $LiIO_3$, KDP (Potassium dihydrogen phosphate), $ZrSiO_4$, $TeO_2$, $Sr_{0.75}Ba_{0.25}Nb_2O_6$, $Sr_{0.5}Ba_{0.5}Nb_2O_6$, $PbMoO_4$, $CdMoO_4$, $PbWO_4$, α-$HIO_3$, $Ca(NbO_3)_2$, $PbCO_3$, $Ba_2NaNb_5O_{15}$, $BaSO_4$ and $Pb_2MoO_5$.

Magnetooptical Materials: Iron, Cobalt, Nickel, Permalloy, Nickel-Iron (various ratios), MnBi Normal (l.t.p.:NiAs), MnBi Quenched (h.t.p.:distorted NiAs), MnAs (NiAs), CrTe (NiAs), FeRh, YIG (Garnet), GdIG (Garnet), $NiFeO_4$ (Spinel), $CoFe_2O_4$ (Spinel), $MgFe_2O_4$, $Li_{0.5}Fe_{2.5}O_4$, $BaFe_{12}O_{19}$ (Hexagonal), $BaZn_2Fe_{12}O_{19}$ (Hexagonal), $RbNif_3{}^{*2}$, $RbNi_{0.75}Co_{0.25}F_3$ (Perovskite)[*3], $RbFeF_3{}^{*4}$, $FeF_3{}^{*5}$, $CrCl_3$ ($BiI_3$), $CrBr_3$ ($BiI_3$), $CrI_3$ ($BiI_3$), $FeBO_3$ (Calcite)[*5], EuO (NaCl), EuS (NaCl), EuSe (NaCl), $EuFeO_3$, $GdFeO_3$, $TbFeO_3$, $DyFeO_3$, $HoFeO_3$, $TmFeO_3$, $YbFeO_3$, $LuFeO_3$, $SmFeO_3$, $YFeO_3$, $LaFeO_3$, $PrFeO_3$, $NdFeO_3$, Eu, $SrTiO_3$, $BaTiO_3$, $KTiO_3$, .$TbAlG^{*1}$, DyAlG, HoAlG, ErAlG, TmAiG and YbAlG.

EXAMPLE 1

Sonoelectroporation Procedural Variants

Five six-well plates containing cultures of NIH/3t3 cells (cell density of $4 \times 10^5$ cells/well) were grown for transfection with plasmid DNA containing the chloramphenicol acetyltransferase gene (CAT). The preparatory incubation was at 37° C. in a 5% $CO_2$ atmosphere. CAT is prepared by Lofstrand Labs of Gaithersburg, Md. MRX 220 is a cationic lipid and its formula is found disclosed in U.S. application Ser. No. 08/391,938, filed Feb. 21, 1995, entitled "Novel Cationic Lipids and the use Thereof", now U.S. Pat. No. 5,830,430. Treatment protocols were as follows:

| Plate | Treatment |
|---|---|
| 1 | Control. Three wells totally untreated; three wells in which cationic lipid MRX 220 + DNA is applied. |
| 2 | Sonoporation only. Six wells treated with MRX 220 + DNA + ultrasound at 0.5 watts/CM² for 30 seconds. (MRX 220 is disclosed in U.S. application Ser. No. 08/391,938, filed Feb. 21, 1995, entitled "Novel Cationic Lipids and the use Thereof", now U.S. Pat. No. 5,830,430.) |
| 3 | Three wells treated with MRX 220 + DNA + ultrasound at 0.5 watts/cm² for 30 seconds + electroporation at 200 mA for 30 secs. using a plus shaped aluminum grid, three wells no energy applied. |
| 4 | Three wells treated with MRX 220 + DNA + ultrasound at 0.5 watts/cm² for 30 seconds + electroporation at 200 mA for 30 sees. using a mesh aluminum grid; three wells no energy applied. |
| 5 | Three wells treated with MRX 220 + DNA + ultrasound at 0.5 watts/cm² for 30 seconds + electroporation at 200 mA for 30 secs. using two copper electrodes; three wells no energy applied. |

(DNA addition precedes energy application by 15 minutes except where specifically noted.) Note: Use of the aluminum electrodes (plates 3,4) involved placement of electrodes in the plate 24 hrs prior to application of energy. The copper electrodes (plate 5) were exposed to the media only through the duration of voltage.

| Data | | OD change (energy input - no energy) |
|---|---|---|
| Transfection Control | | 66.0 (cationic lipid/DNA only) |
| Plus shaped Al electrode | (+ elect.) | 88.7 |
| | (− elect.) | 20.3 |
| Mesh Grid Al | (+ elect.) | 65.7 |
| | (− elect.) | 152.1 |
| Copper electrodes | (+ elect.) | 41.1 |
| | (− elect.) | 93.4 |

As can be seen, enhancement of cationic lipid mediated transfection as attributable to the combination of ultrasound and electroporation is seen most prominently with the plus-shaped aluminum electrode.

EXAMPLE 2

Robotic sonoelectroporation is used to transfect a variety of different cells (e.g, epithelial, endothelial, renal, cardiac and hepatic cells) with the telomerase gene. (The plasmid vector would be linearized with an appropriate restriction endonuclease.) These cells are then studied for telomerase gene expression, aging, etc. Sonoelectroporation is used to optimize telomerase gene expression and then to screen compounds that might be used to target telomerase to turn the gene "on" and "off".

EXAMPLE 3

A linear strand of DNA bearing "sticky ends" is constructed. (E:g., the IF3 and telomerase genes would have linkers attached to their ends using T4 DNA ligase. The linkers would overlap the ends of the vector DNA by standard recombinant technique. The whole construct would then be ligated in place.) bearing Initiation factor-3 (sonoporation "on switch"). Varying constructs are prepared with sticky ends targeted to different parts of the genome. The sticky ends select for non-coding regions upstream of target genes. Cells are incubated with the "on switch" constructs at 37° C. for one hour. Robotic sonoporation, sonoelectroporation and sonooptical modulation are then applied to different cell cultures at different time points following incubation of the cells with the "on switch." The target gene products are identified with RT-PCR. This process proves invaluable in identifying the presence of certain target genes as well as localizing them to certain regions in the genome by virtue of the site directed sonoporation "on switches."

EXAMPLE 4

Figure 7A:
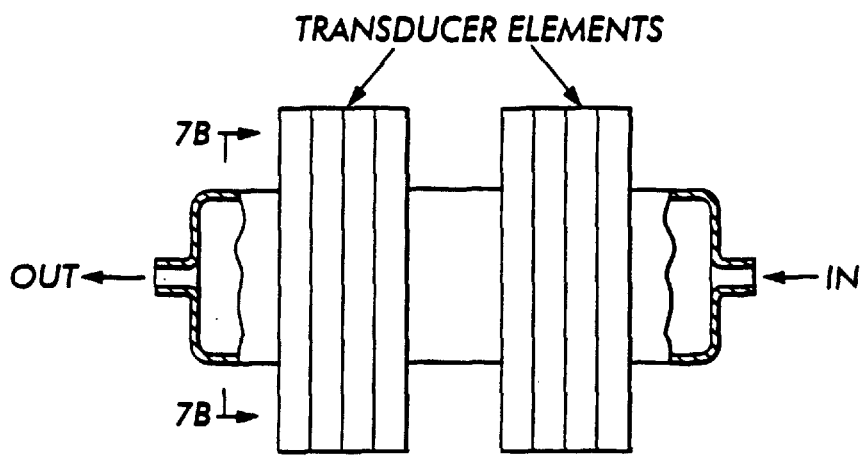
FIGS. 7A, 7B and 7C illustrate a sonoelectroporation bioreactor and the relative positioning of ultrasound and electrical elements, as well as a scaffold element through which cells flow during exposure to applied energy.
Figure 7B:
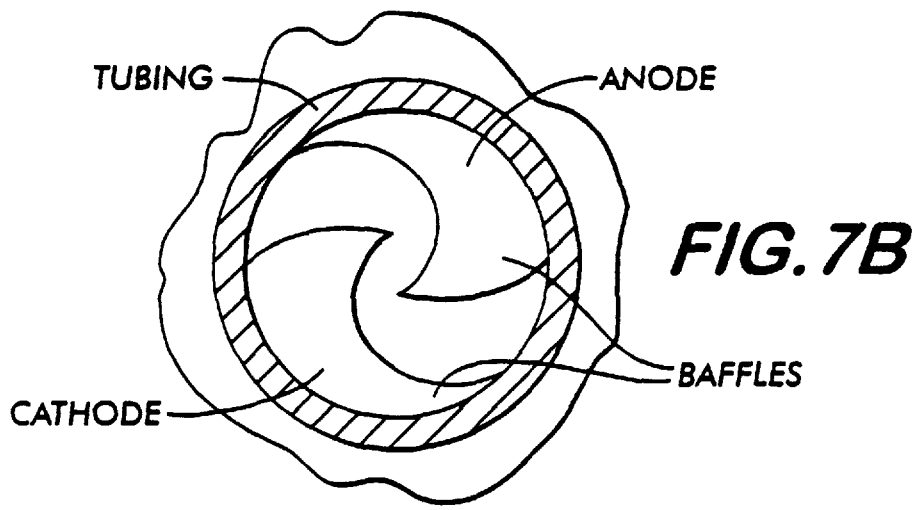
Figure 7C:
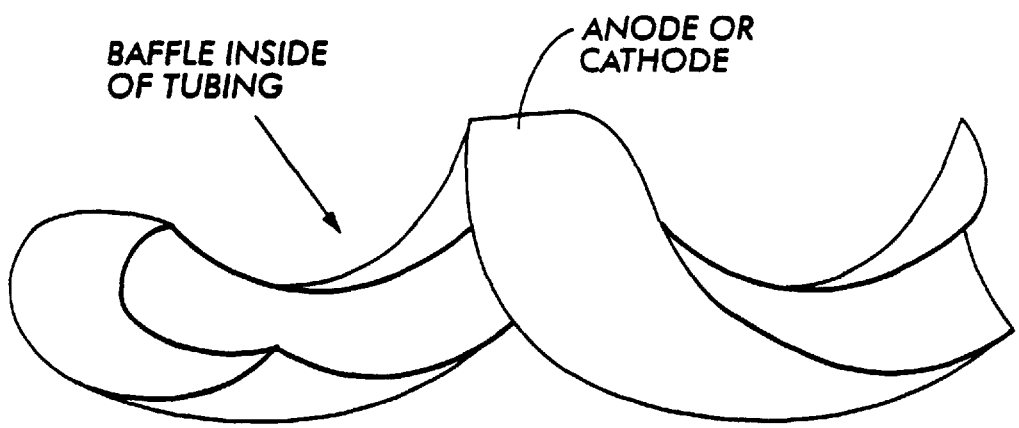
Figure 8:
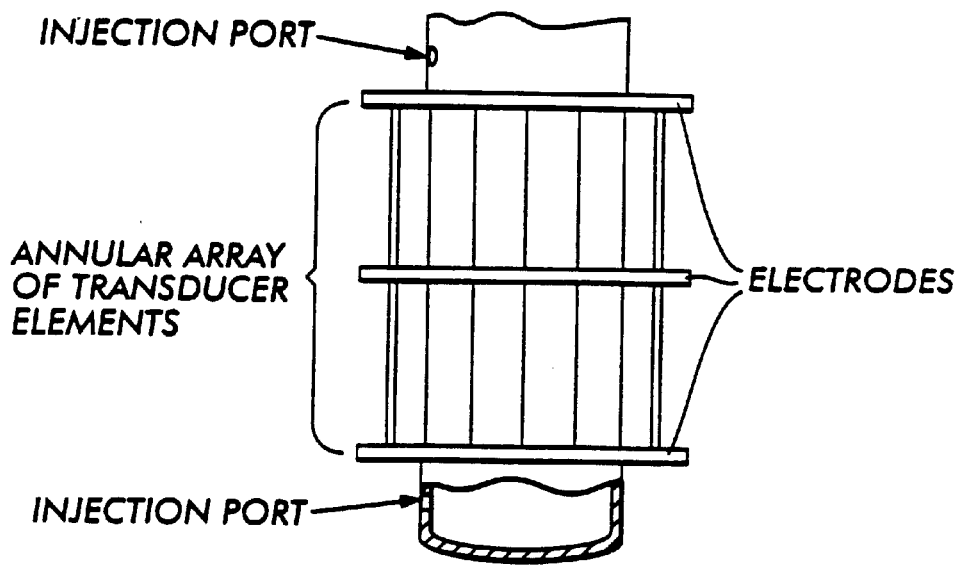
FIG. 8 illustrates an endoscopic sonoelectroporation device in accordance with the present invention.

A flow-through bioreactor probe is used to transform yeast, bacteria and human cells. The flow-through bioreactor probe is designed as in FIGS. 7A, 7B and 7C. The device comprises an outer array of acoustic elements and an inner electrically conductive polymer scaffold. In FIG. 7A, two linear arrays are shown although annular arrays may also be used as shown in FIG. 8. Inside the tubing, there are two baffles electronically insulated from each other. The baffles are connected to an external voltage source. One baffle is the anode and the other is the cathode. The baffles are arranged such that, when a suspension of cells pass through the scaffold, they encounter a nearly uniform electric field. The cells (such as, e.g. HeLa) flow through the scaffold elements of the bioreactor probe and encounter an electric field. Ultrasound is applied simultaneously with the annular array of elements as the cells enter the electric field. The scaffold is designed to be electrically conductive and also have an acoustic impedance similar to the aqueous milieu surrounding the cells. Typically the flow rate through the bioreactor is adjusted such that the cells are exposed to a uniform and pre-determined amount of ultrasound and electrical energy. Typically the electrical energy is in the range of 1 to 500 V/cm² (preferably about 50 Volts/cm²) and the ultrasound energy is in the range of 0.1 to 10 Watts/cm² (preferably about 1 Watt/cm²). The flow rate and scaffold are designed to control the duration of time to which the cells are exposed to ultrasound and electrical energy. The typical duration of exposure is from about 1 millisecond to 1,000 seconds, more usually from 5 to 120 seconds, with from 10 to 30 seconds being preferred. The ultrasound energy is preferably continuous but may be pulsed. The electrical energy is preferably pulsed and phase modulated to interact with the ultrasound. As the cells flow through the scaffold, exposure to sonoelectroporation enhanced transfection efficiency.

EXAMPLE 5

E. coli is grown to a concentration of 10 million cells per ml (e.g., in a medium of E. coli HB 101 grown to early log phase in LB broth). The bacterial cells are mixed into a suspension of Luria-Bertani broth cell culture media containing 100 million plasmids per ml encoding the gene for vascular endothelial growth factor (VEG-F). The cells and DNA suspension are infused through the bioreactor probe at a rate such that each aliquot of cells receives on average a 30 second exposure to sonoelectroporation. Continuous wave ultrasound is provided at a frequency of 100 kHz at 1 Watt per cm² and the electrical energy is provided at 50 Watts per cm² with pulses of 50 microseconds duration applied temporally to correspond with the peak negative amplitude of each ultrasound pulse. The cells in the effluent after passage through the bioreactor are grown in culture for 72 hours and harvested. The VEG-F is harvested from the bacteria, isolated and purified. Sonoelectroporation results in higher yields of VEG-F from the bacteria than other transfection techniques.

As one skilled in the art would recognize, sonoelectroporation bioreactors can be used for autologous cells and incorporated into plasmapharesis. This technology can be used to provide high throughput tansfection for cytokines, growth factors, antibodies and a host of genes. The bioreactor and scaffold ensemble can be provided sterile and constructed of disposable materials. For use with plasmapharesis and autologous human cells, after a single use the unit can be disposed. Alternatively, the unit can be sterilized and reused.

The sonoelectroporation bioreactor also has applications for fermentation with yeast. Sonoelectroporation can be used to increase the yield of alcohols during fermentation and the yield of a variety of products via fermentation.

EXAMPLE 6

An endoscopic sonoelectroporation device is shown in FIG. 8. The endoscope is equipped with an ensemble of transducer elements capable of both imaging with pulsed ultrasound and continuous wave insonation for sonoelectroporation. The transducer elements for imaging and sonoporation may be the same or different. When they are separate (i.e., different elements), typically the imaging elements are higher frequency and the sonoporation elements are lower frequency. Typically, imaging is performed from 1 to 30 MHz with from 2.5 to 20 MHz more preferred. The sonoporation frequency ranges typically from 20 kHz to 20 MHz with from 100 kHz to 5 MHz more preferred. The voltage ranges from about 1 millivolt to 200 volts. The endoscope is positioned over the body part to be treated with sonoelectroporation and ultrasound, and electrical energy is applied to the target tissue. The genetic materials may be administered intravenously, interstitially or topically. Injection can also be performed via injection ports which may be incorporated into the sonoelectroporation endoscope. Typically, the sonoelectroporation energy is administered to the tissue for a period of anywhere from about a millisecond to up to 1000 seconds, but most usually from 1 to 100 seconds duration.

EXAMPLE 7

A 24 French size sonoelectroporation endoscope is passed into the esophagus of a patient with esophageal carcinoma. The probe is equipped with a broad-band imaging transducer with frequency range from 3.75 to 7.5 MHz and 1.25 MHz continuous wave therapeutic elements. Imaging is used to position the transducer over the tumor, which in this patient is within the mid-portion of the distal esophagus, representing an adenocarcinoma. The patient is grounded by lying on a surgical table made of stainless steel. The patient is injected intravenously with a 10 ml solution containing lipoplex entrapping 1 mg of plasmid encoding the gene for interleukin-2 (IL-2). The lipoplex is composed of dipalmitoylphosphatidylethylcholine/dioleolylphosphatidylethanolamine (1:3 ratio of DPEPC to DOPE), lipids from Avanti Polar Lipids, Alabaster, Ala., with perfluorohexane (PFC) that had previously been prepared by mixing the lipids and PFC on a Capmix dental amalgamator in sealed vial at 4,200 r.p.m. During and after the injection, the tumor is monitored with ultrasound imaging using second harmonic technique, in this case transmit frequency =3.75 MHz and receive frequency =7.5 MHz. As the acoustically active lipoplex flows through the microvessels within the tumor interstitium, the signals are received by the transducer at 7.5 MHz. The system is designed so that pulses of 1.25 MHz continuous wave ultrasound energy at 1 watt per $cm^2$ are then applied when the acoustically active gene/lipoplex passes into the tumor's microvessels. Electrical energy is discharged simultaneously with the continuous wave ultrasound at 50 Volts/$cm^2$. The continuous wave ultrasound is triggered at intervals of 500 milliseconds on and 500 milliseconds off. Second harmonic signals are used as the trigger initiator for administration of each train of continuous wave ultrasound, i.e., the continuous wave ultrasound is turned off until receipt of the second harmonic signals. The electrical energy is pulsed at 50 microsecond intervals. The center of each pulse is adjusted to coincide with the peak negative amplitude of continuous wave ultrasound pulse. The electrical pulses are turned off until the continuous wave pulses are turned on. In this fashion, sonosonoelectroporation is administered to the patient endoscopically until the second harmonic signals have returned to baseline, in this case for about 30 minutes, during which time sonoelectroporation may have been in the active "on" mode for about 5 minutes. The patient has highly efficient transfection of the esophageal tumor with IL-2. Local production of cytokine within the tumor improves tumor control in this patient. As one skilled in the art would recognize, this new technology can be used with a wide variety of different genes and anti-sense constructs (e.g., anti-sense to the Ras oncogene) and also be incorporated into other treatment programs such as conventional radiation therapy and chemotherapy.

EXAMPLE 8

Figure 9:
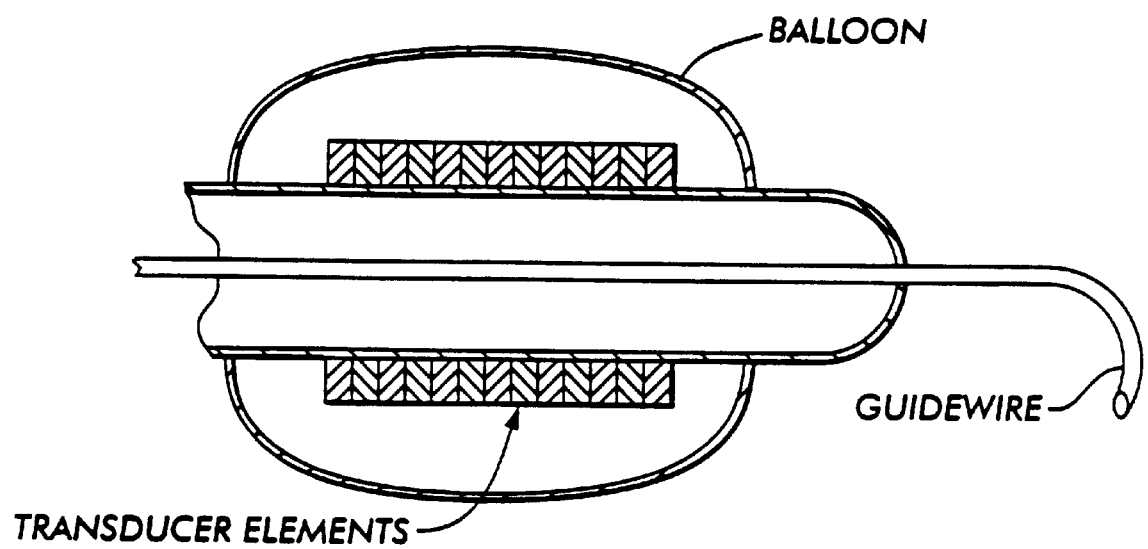
FIG. 9 illustrates a sonoelectroporation balloon catheter in accordance with the present invention.

An sonoelectroporation balloon catheter is designed as shown in FIG. 9. The catheter is 7 French and has a 7 millimeter balloon. The balloon is composed of a electrically conductive material and functions as an anode. The balloon is coated with cationic lipid and genetic material. The tip of the catheter within the balloon contains a 1 MHz continuous wave ultrasound transducer. An 0.035 inch guidewire is placed under fluoroscopic control across a tight stenosis due to arteriosclerotic plaque involving the left main coronary artery. The sonoelectroporation catheter is positioned with the balloon centered across the stenosis. The balloon is inflated to 9 atmospheres using degassed saline containing convention surfactants and anti-foaming agents. As the balloon is inflated the continuous wave ultrasound is activated at 2 Watts per $cm^2$ for 30 seconds and electrical discharges are also maintained at 25 Volts per $cm^2$ during this time. One patient is treated with the gene for VEG-F which is affixed to the surface of the catheter via the cationic lipids. Another patient is treated with an anti-sense construct to fibroblast growth factor (anti-FGF). Sonoelectroporation administered at the time of angioplasty results in improved results. In the case of VEG-F, catheter mediated sonoelectroporation results in increased local expression of VEG-F and in turn, angiogenesis and increased vascularization of myocardial tissue. In the case of anti-FGF, sonoelectroporation improves tissue penetration and nuclear integration of the anti-sense construct such that there less propensity for restenosis.

EXAMPLE 9

Figure 10:
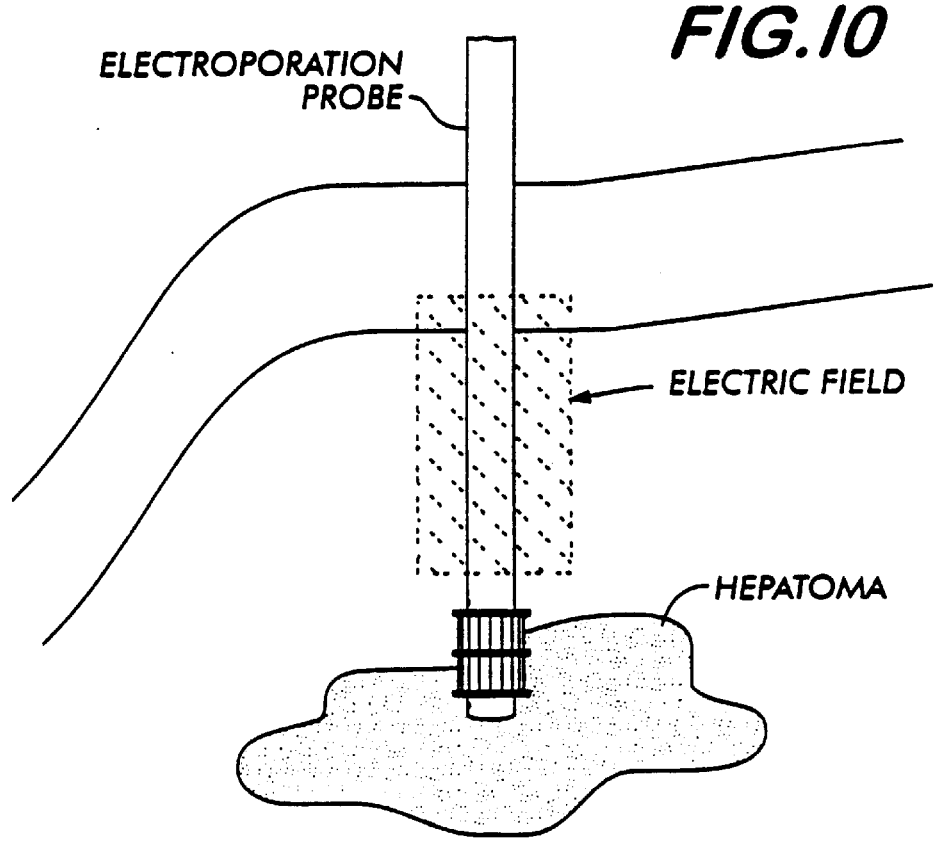
FIG. 10 illustrates a sonoelectroporation needle probe in accordance with the present invention.

An sonoelectroporation probe is shown in FIG. 10. In this case, a needle containing both an electrode and a piezoelectric element is provided. The sonoelectroporation needle may be provided in sizes as small as 22 gauge and potentially smaller using microelectronics or larger up to 10 gauge. A 16 gauge sonoelectroporation needle probe is directed into a hepatoma (liver tumor) of a patient under guidance of computed tomography. The patient is administered an interstitial (i.e., intratumoral) dose of retrovirus via injection through the sonoelectroporation probe containing a total of approximately 100 micrograms of DNA (total volume =2.5 ml) encoding the gene for HLA-B7. The interstitial injection of gene is performed slowly over a period of about 3 minutes during which time the patient is instructed to breath gently. During injection and for a period of two minutes thereafter continuous wave 1.0 MHz ultrasound is applied via the probe at 1.0 watts per $cm^2$ and electrical energy is applied at 100 Volts/$cm^2$. Sonoelectroporation is applied at intervals of two seconds on and two seconds off throughout a total period of five minutes. Sonoelectroporation results in increased transfection efficiency in the hepatoma. The patient's immune system recognizes the HLA-B7 antigens that are now expressed in the tumor and mounts an effective immune response against the tumor.

EXAMPLE 10

Figure 11:
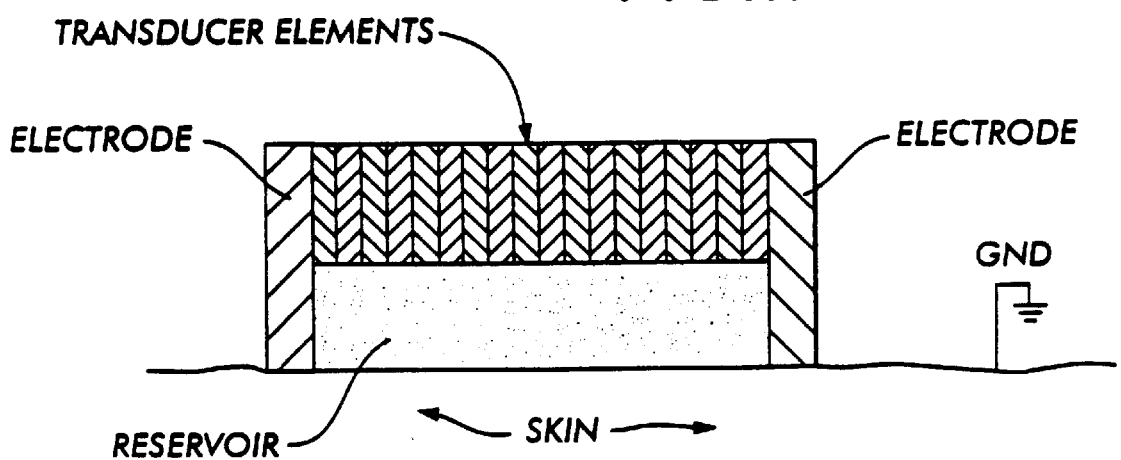
FIG. 11 illustrates a transcutaneous sonoelectroporation device in accordance with the present invention.

A transcutaneous sonoelectroporation device is shown in FIG. 11. The device comprises piezoelectric and electrode face elements which are applied to the skin. A reservoir can be attached to the surface of the transducer face that contains the genetic and carrier materials. Alternatively, the genetic materials can be incorporated into an acoustically and electrically active gel. Such a gel can be prepared by formulating silicone gel with lipids and counterions, for example, 10 parts by weight silicone and 0.2 parts by weight cationic lipids (e.g. 3:1 DPEPC/DOPE) with 200 mg per ml of sodium chloride. The genes may be incorporated into this carrier gel. Additionally, various penetration enhancers such as are well known in the art may be incorporated into the gel. The device can be applied to the skin for different time duration, typically ranging from about 10 seconds to 30 minutes. Additionally, the device may be equipped with a portable power supply so that it can be worn by the patient during daily activities. In this manner sonoelectroporation can be applied periodically throughout the day to deliver physiologic supply of genetic materials. The device is useful for transcutaneous delivery of a variety of different genetic materials including DNA vaccines growth factors, insulin and anti-sense materials.

IV. Conclusion

The present invention is not limited to the specific, presently preferred embodiments disclosed above. Accordingly, except as they may be specifically so limited, the scope of the protection of the following claims is not limited to the presently preferred embodiments disclosed herein, but rather is intended to cover all obvious modifications thereof.

We claim:

1. A method comprising applying ultrasonic energy in combination with electrical energy to cells to enhance cell uptake of a desired material and to enhance subsequent gene expression, wherein said ultrasonic energy and said electrical energy are applied with a sonoelectroporation transducer comprising electrodes within a transducer ensemble.

2. A method as recited in claim 1, wherein said electrical energy comprises one or more electrical impulses and said electrical energy and said ultrasonic energy are generated by the sonoelectroporation transducer, and said electrical energy and said ultrasonic energy are applied sequentially to the cells.

3. A method as recited in claim 1, wherein said electrical energy comprises one or more electrical impulses and said electrical energy and said ultrasonic energy are generated by the sonoelectroporation transducer and said electrical energy and said ultrasonic energy are applied simultaneously to the cells.

4. A method as recited in claim 1, wherein an electric field in the range of about 1 to 10 kV/cm is applied to the cells.

5. A method as recited in claim 4, wherein the electric field in combination with ultrasound creates a reverse pore through membranes of the cells.

6. A method as recited in claim 1, wherein the sonoelectroporation transducer includes an acoustic element operating at a frequency of between about 10 kHz and about 10 MHz.

7. A method as recited in claim 1, wherein the mode of operation of the ultrasonic energy, continuous or pulsed wave, is changed for different applications.

8. A method as recited in claim 7, wherein the pulsed wave mode is used for applications of energy to single cells, unilamellar cell cultures, perfused organs, thick tissues or whole bodies.

9. A method as recited in claim 8, wherein a pulse duration of between about 10 $\mu$s to about 10 ms is used.

10. A method as recited in claim 8, wherein a pulse repetition frequency in the range of from about 0.5 Hz to about 1 kHz is used.

11. A method as recited in claim 7, wherein continuous wave mode is used for applications of energy to single cells, unilamellar cell cultures, perfused organs, thick tissues or whole bodies.

12. A method as recited in claim 7, wherein the acoustic energy intensity, defined in terms of $I_{SATA}$, or spatial average/temporal average intensity, is in the range of from about 1.0 gW/$cm^2$ to about 100 W/$cm^2$.

13. A method as recited in claim 12, wherein the energy intensity is about 0.1 to 5 W/$cm^2$.

14. A method as recited in claim 1, wherein a frequency range of from about 100 kHz to about 2 MHz is used for the electrical energy.

15. A method as recited in claim 14, wherein an electric field intensity in the range of from about 1 V/cm to about 100 kV/cm is used.

16. A method as recited in claim 15, wherein an electric field intensity in the range of from about 50 V/cm to about 10 kV/cm is used.

17. An apparatus for application of ultrasonic energy in combination with electrical energy to cells to enhance cell uptake of a desired material comprising a sonoelectroporation transducer comprising electrodes within a transducer ensemble to generate said ultrasonic energy and said electrical energy.

18. The apparatus of claim 17, wherein said sonoelectroporation transducer generates electrical energy as one or more electrical impulses.

19. The apparatus of claim 18, wherein said sonoelectroporation transducer applies said ultrasonic energy and said electrical energy sequentially to the cells.

20. The apparatus of claim 18, wherein said sonoelectroporation transducer applies said ultrasonic energy and said electrical energy simultaneously to the cells.

21. The apparatus of claim 17, wherein said sonoelectroporation transducer applies ultrasonic energy in combination with electrical energy to cells to enhance subsequent gene expression.

22. The apparatus of claim 17, wherein said sonoelectroporation transducer applies an electric field in the range of about 1 to 10 kV/cm to the cells.

23. The apparatus of claim 22, wherein said electric field in combination with said ultrasonic energy creates a reverse pore through membranes of the cells.

24. The apparatus of claim 17, wherein the sonoelectroporation transducer includes an acoustic element operating at a frequency of between about 10 kHz and about 10 MHz.

25. The apparatus of claim 17, wherein the sonoelectroporation transducer includes an acoustic element that changes mode of operation for different applications to apply the ultrasonic energy in continuous wave or pulsed wave.

26. The apparatus of claim 25, wherein said acoustic element applies the pulsed wave mode of energy to single cells, unilamellar cell cultures, perfused organs, thick tissues or whole bodies.

27. The apparatus of claim 26, wherein said acoustic element produces a pulse duration of between about 10 $\mu$s to about 10 ms.

28. The apparatus of claim 26, wherein said acoustic element produces a pulse repetition frequency of from about 0.5 Hz to about 1 kHz.

29. The apparatus of claim 25, wherein said acoustic element applies the continuous wave mode of energy to single cells, unilamellar cell cultures, perfused organs, thick tissues or whole bodies.

30. The apparatus of claim 25, wherein said acoustic element produces acoustic energy intensity, defined in terms of $I_{SATA}$, or spatial average/temporal average intensity, in the range of from about 1.0 $\mu$W/cm$^2$ to about 100 W/cm$^2$.

31. The apparatus of claim 30, wherein said acoustic element produces the energy intensity at about 0.1 to 5 W/cm$^2$.

32. The apparatus of claim 17, wherein said electrodes produce a frequency range of from about 100 kHz to about 2 MHz for the electrical energy.

33. The apparatus of claim 32, wherein said electrodes produce an electric field intensity in the range of from about 1 V/cm to about 100 kV/cm.

34. The apparatus of claim 33, wherein said electrodes produce the electric field intensity in the range of from about 50 V/cm to about 10 kV/cm.

\* \* \* \* \*

UNITED STATES PATENT AND TRADEMARK OFFICE
CERTIFICATE OF CORRECTION

PATENT NO. : 6,627,421 B1 Page 1 of 1
DATED : September 30, 2003
INVENTOR(S) : Evan C. Unger, Yunqiu Wu and Thomas McCreery It is certified that error appears in the above-identified patent and that said Letters Patent is hereby corrected as shown below:

Column 7,
Lien 33, insert -- be -- after "may";

Column 12,
Line 7, delete "1 W/cm$^2$ to 1 kW/cm$^2$" and insert -- 1 mW/cm$^2$ to 1 kW/cm$^2$ -- therefor;

Column 13,
Line 65, delete "α-Manganese." and insert -- α-Manganese, -- therefor.

Column 14,
Line 25, delete "$(C_6H_{12}O_6)_2$NaBr $H_2O$," and insert -- $(C_6H_{12}O_6)_2$NaBr · $H_2O$, -- therefor;

Column 15,
Line 59, delete "(E:g.," and insert -- (e.g., -- therefor;

Column 17,
Line 4, delete "tansfection" and insert -- transfection -- therefor;

Column 20,
Line 33, delete "gW/cm$_2$" and insert -- μW/cm$_2$ -- therefor.

Signed and Sealed this

Twenty-fifth Day of November, 2003

JAMES E. ROGAN
*Director of the United States Patent and Trademark Office*